United States Patent

Araki et al.

[11] Patent Number: 5,948,650
[45] Date of Patent: Sep. 7, 1999

[54] GENETIC VARIETY IDENTIFYING METHOD IN HOPS

[75] Inventors: Shigeki Araki; Yohichi Tsuchiya, both of Yaizu, Japan

[73] Assignee: Sapporo Breweries Ltd., Tokyo, Japan

[21] Appl. No.: 08/809,297

[22] PCT Filed: Jul. 26, 1996

[86] PCT No.: PCT/JP96/02121

§ 371 Date: May 6, 1997

§ 102(e) Date: May 6, 1997

[87] PCT Pub. No.: WO97/05281

PCT Pub. Date: Feb. 13, 1997

[30] Foreign Application Priority Data

Jul. 28, 1995 [JP] Japan ................................. 7-211328
Apr. 30, 1996 [JP] Japan ................................. 8-130586

[51] Int. Cl.[6] ............................. C12P 19/34; C07H 21/04; C07H 21/00
[52] U.S. Cl. ....................... 435/91.2; 435/91.1; 536/22.1; 536/24.3; 536/25.3
[58] Field of Search ............................... 536/22.1, 24.3, 536/25.3; 435/91.1, 91.2

[56] References Cited

PUBLICATIONS

Pillay et al. Chloroplast DNA between cultivated hop, *Humulus Iupulus* and the related species *H. japonuicus* Theor. Appl. Genet vol. 89, pp. 372–378, 1994.

Pillay et al. Random amplified polymorphic DNA (RAPD) markers in hop, *Humulus lupulus*: level of genetic variability and segregation F1 progeny, Theor. Appl. Genet. vol. 92, pp. 334–339, 1996.

Williams et al. DNA polymorphisms amplified by arbitrary primers are useful as genetic markers, Nucleic Acids Research vol. 18(22), pp. 6531–6535, 1990.

Plant Breeding, vol. 113 (1994) G. Mosges et al., "Genetics Fingerprinting of Sunflower Lines and F1 Hybrids using Isozymers, Simple and Repetitive Sequences as Hybridization Probes, and Random Primers for PCR", pp. 114–124.

Methods in Molecular and Cellular Biology, vol. 5 (1994) Perry B. Gregan, et al., "Microsatellite Fingerprinting and Mapping of Soybean" pp. 49–61.

Theor. Appl.Genet., vol. 85 (1992) S. He et al., "Detection of DNA Sequence Polymorphisms Among Wheat Varieties" pp. 573–578.

Euphytica, vol. 80 (1994), H.L. Ko et al. "Random Amplified Polymorphic DNA Analysis of Australian Rice (Qryza Sativa L.) Varieties" pp. 179–189.

J. American Society Hort. Sci., vol. 119(4) (1994) J. F. Hancock et al. "Randomly Amplified Polymorphic DNAs in the Cultivated Strawberry FragariaXananassa" pp. 862–864.

*Primary Examiner*—Ardin H. Marschel
*Assistant Examiner*—Joyce Tung
*Attorney, Agent, or Firm*—Oblon, Spivak, McClelland, Maier & Neustadt, P.C.

[57] ABSTRACT

This invention is a method for identifying hop varieties based on polymorphism in genetic sequences of hop varieties. Specifically, polymorphic regions of hop DNA are amplified by performing a polymerase chain reaction using an identifying primer designed to amplify regions comprising polymorphism in the base sequences of different varieties, and the amplified DNA fragments are analyzed. In this way, hop varieties can simply and accurately identified.

13 Claims, 5 Drawing Sheets

```
                        5'   B72
Hallertauer Tradition   GGCGATTCTGCAAGAGACACAACGCAGACAAGAAATTTGAATAACA
Shinshu Wase            ********************************C*********

B72WF2
TAATCGAGAGGGGGTTTGCTCTCGAGTCCCTCCTAGACACCTACATAGCAATTGCTACAATTTCCTAGTGT
***********************************************************************

CCGCAAATATTGTAGGGGTTACTAA-TGGATTTATTGTTTACATCTGTTGCATTCTTTTATGTAAATGATG
*T********************** **********************************************
```

```
ATGATGAGATTCCATATGAATGAGAGTCTTTATAAGCTAAAAATTTAATGGCATGCATTGTATCCCAAGG
****C***************-C-************************************T*****

CAAATGGTCATGCAGATGCAATGGAGTACTGAATAAATTAAATTAAACTGGTTTTACAGACGCTGTTGAC
*****************************TG***********************C***************

B72WR2
AAACAAAATAGGTAATACCAGAAGCTTACCTTGCTGTCAGGAGCAAATTTTAAACGAACAGCTTTCCAGT
***********************************************************************

CAGACACGTCCTCATCGGTGCCACCACTTCCAGTTTCACTGCTTGGTTCCACAGGTTTCTCAAGTACGTT
***********************************************************************

CTTCCGGAACTTCTCTAGTCTTGCTAGAACCTGAAGGAAACGTTAACCAGCAAAGTTGGTAATTGGAAAC
*********************************************A************************
                                                                      3'
TTAATTAGCAAATAATGCTAATGTGAAGAGCAATACATCAAATTGTTTTATATGCAGAATCGCC
***********************************************************
                                                              B72
```

*FIG. 2*

5'-GGTCAGGCACCATGTACTAGCTGGCGCGACAGTCCCATGCAGAGCTATTCCGGTCCGTAGTAGATTACTTAACATCTCCCATTCTAG
       A                                  C

ATCACACCGAATGGGATCCAAGCCCTCTCTGCGTATACATTCTTACTTTCTGAATGGTTGGGACGAGCCCACTCCACATGAGGTGCATTACT

TGTTCGATCTCAGGACCAACCCCTCTCACAACAACTCAGGCTTTTTCCACTTCTATNATAGGCATAGGGGGATTACATACCTCAAGCGTATTC

TCATAGGTCGAATGCCGGGAGGTATCATAAGGGATACTTCCTCACCTTGGACATCGAGGCCAACAAATTTGGGCCTTAACTCGNTCGGGGTCCA

TTTGAGGGACCATTGCCTACTGAGGAGATGNTCAATCGGNCCAAGNAGTTGGCTAACATGAGTTCTAAAGATAAGGATGTNAAAAGGTTGGTCA

CACTTGACCTCCTTCAGATGGTTGCCTTGGGTGCCTGACC-3'
    D                          B

*FIG. 4*

5'-CGCCCTGCAGTAGCTTCCTGTAAGTTTACAAGGGACTTGATACAACCTCTAGGTGCAATCAAGTTAGCCCTCACAATGGGA
         └─────────A─────────┘        └─C─┘

GAGAAACCAAGACAAACCACTATAATGACAAACTTTGTCGTGGTAGATTGTGCCTCAGCCTTAAATGCGGTATTAGAAAGACCTTC

CCTAAGAGAATTGAAGGGGAATAACCTCAGTATAAACACTTGGCCATAAAATTCCCAACTCTTGGAGGAATAGCGAGCGTGAAAGGGG

AATAGAAGGAAGCAAGGGAATGTTATAACACGTCCCTCCACACAGTCATGAAACTGCCATTACCCATGTGATGGTGGTGCATGGA

GGTGCAAACTCACATGACTTAGACCCTCGAGTTGTTGAGGAGATCAGAATCAAAATGGATAACAGAGAGATAAATGAGCTATGCCT

AAAAAAAATCAGAAAATTAGAAGAGCAGTGCAAAAAAATCTATAGAAGTGTTCTACTGCAGGGCG-3'
                         └────────D─────────┘└─────B─────┘

FIG. 5

GENETIC VARIETY IDENTIFYING METHOD IN HOPS

FIELD OF THE INVENTION

This invention relates to a method of identifying hop varieties, and in particular, to an identifying method which utilizes genetic engineering technology.

BACKGROUND OF THE INVENTION

Hops gives beer its unique aroma and bitterness, and also helps to sediment out excess protein and suppress bacterial proliferation. However, as the extent to which hops act in this way varies mainly according to the variety, it is necessary to identify hop varieties in order to manufacture beer of consistent quality and develop new beers.

Conventionally, the identification of hop varieties was based on their constituent components, e.g. bitter components ($\alpha$ acid/$\beta$ acid cohumulone/humulone, colupulone/lupulone) and essential oil components (farnesene, caryophyllene).

However, in addition to the fact that this identifying method based on bitterness and oils requires a great amount of effort for measuring all the components, it was also unable to determine the varieties precisely because, even for the same variety, these components vary widely depending on the harvesting location and year. Due to recent progress in genetic engineering, various attempts have been made to elucidate sequences of chromosomes depending on the plant species, and based on the base sequences found, to identify strains from differences in genetic information between different plants or varieties of the same plant, i.e. from the polymorphism of DNA sequences.

An identification of plant variety based on this kind of polymorphism is reliable because the DNA sequence itself is not easily affected by environmental influences, and is therefore invariant.

In this regard, the present invention provides a reliable and simple method of identifying hop varieties using the aforesaid genetic technique.

DISCLOSURE OF THE INVENTION

The method of identifying hop varieties according to this invention detects this polymorphism genetically based on differences in DNA sequences between varieties. Specifically, portions of the DNA sequence of hops which show polymorphism are amplified by a polymerase chain reaction (referred to hereafter as PCR) using an identifying primer, and the varieties are then identified by analyzing this amplified DNA.

To use the above method, it is necessary to understand the polymorphism of DNA between hop varieties.

The term polymorphism specifically covers differences in the genetic sequence due to insertions, deletions or substitutions. The length of the sequence involved may be 1 bp, or several tens of bp or more, but is preferably in a range from several bp to several tens of bp.

This sequential polymorphism between varieties may be detected by determining sequences of parts corresponding to chromosome DNA for each variety, and then performing a comparative analysis on the sequences. A simpler method however is to use the RAPD (Random Amplified Polymorphic DNA) technique developed by Williams et al (Nucleic Acids Research, Vol. 18, p. 6531, 1990).

This RAPD technique detects polymorphism between unknown DNA sequences using PCR. Specifically, primers of low specificity comprising a relatively short synthetic oligonucleotide of about 10 bases are mixed with a plurality of DNA types, and PCR is performed.

When the DNA sequence of the hop comprises a sequence which is fully or partially complementary to the primers, the primers anneal with the full or partial complementary sequence, and the portion enclosed between primers is synthesized and is amplified. When there are differences in the sequence such as insertions or deletions in the DNA within the portion enclosed between primers, PCR amplified fragments of different size are obtained depending on the variety. Further, when one variety comprises a sequence with which a primer anneals and another variety does not, PCR amplified fragments are obtained only for the first variety. The polymorphism may then be detected by fractionation, e.g. by electrophoresis.

The RAPD method may be used not only to detect polymorphism according to this invention as described above, but also to select primers that can detect polymorphism by PCR, i.e. as a primer designing method.

All polymorphic regions in the DNA of hop varieties detected by the RAPD method are addressed by the method of this invention. Also, all primers which can amplify polymorphic regions detected by the RAPD method may be utilized as identifying primers according to this invention.

The identifying primer of this invention developed by the above method may be one type of synthetic oligonucleotide, or two or more types of synthetic oligonucleotide.

The length of this synthetic oligonucleotide is within the range 6–40 and preferably 10–21. Specifically, it is convenient to use an oligonucleotide comprising the base sequence indicated by SEQ.ID No.: 1–14 in the sequence listing.

A second method for designing an identifying primer according to this invention comprises the following steps.

This method first determines the base sequence of the amplified fragment obtained by the polymerase chain method using an identifying primer (e.g. a primer which can amplify the polymorphic region detected by the PAPD method above, referred to hereafter as a primary primer). Finally, two identifying primers are synthesized which respectively complement positions a predetermined interval apart in the above polymorphic sequence fragment, so as to produce an amplified fragment which permits the polymorphic sequence to be identified by a primary primer with high reproducibility and simplicity.

In other words, according to the above method, the identifying primer may be selectively designed based on the polymorphic sequence and surrounding sequences.

The aforesaid primary primer may be an oligonucleotide comprising a base sequence described in SEQ.ID Nos: 1–14 of the sequence listing.

For example, the first identifying primer sequence may be designed so that either one or both primers comprise all or part of the polymorphic sequence mentioned above.

When strain identification is performed by the aforesaid primers, and a strain comprising the selected polymorphic sequence is used, DNA amplification takes place due to PCR as the strain comprises the complementary sequence, and a specific amplified DNA is obtained. On the other hand, when a strain not comprising the polymorphic sequence is used, amplified DNA is not produced even when PCR is performed as the strain does not comprise the complementary sequence. In this case therefore, it is possible to identify the strain from the presence or absence of the amplified fragment.

The sequence of the second identifying primer may be designed such that the two types of primer are situated respectively upstream and downstream of the polymorphic sequence.

When strain identification is performed using the above identifying primers, amplified DNA having a different internal base sequence depending on the strain, and in some cases a different size, is produced by PCR. The strain may then be identified from the migration pattern obtained by fractionating the amplified DNA, using electrophoresis, electrophoresis after digesting with a restriction enzyme if necessary, denaturing gradient gel electrophoresis or temperature gradient gel electrophoresis.

A third identifying primer may be designed to comprise a primary primer sequence at the 5' end, the base sequence in a polymorphic area joined to this sequence comprising 5–20 bases linked together. Strain identification using this identifying primer is useful when for example there is a polymorphic sequence at a position to which the primary primer is complementary. In other words, the polymorphic sequence may be detected with greater specificity than by the primary primer alone by attaching the sequence of 5–20 bases to it.

Further, any identifying primer not comprising this type of sequence may also conveniently be used as a hop identifying primer provided that it is designed according to the above method.

Specifically, the identifying primer designed according to the above method may be a synthetic oligonucleotide comprising a base sequence described in SEQ.ID Nos. 15–40 of the sequence listing, or a suitable combination of two synthetic oligonucleotide each comprising part of this base sequence, as may be appropriate.

Alternatively, the identifying primer may be a synthetic oligonucleotide which comprises part of the base sequence of genome DNA between a position where the base sequence of SEQ.ID No: 15 (17, 19, 21, 23, 25, 27, 29, 31, 33, 35, 37, 39) is annealed to genome DNA, and a position where the base sequence of SEQ.ID No: 16 (18, 20, 22, 24, 26, 28, 30, 32, 34, 36, 38, 40) is annealed to genome DNA.

According to this method of designing the second identifying primer (i.e. with this composition), it is possible to determine the base sequence of a region which exhibits polymorphism, and hence the method provides a primer which can identify strains more reliably.

In this way, by performing a comparative analysis of DNA between strains based on genetic techniques according to the strain identifying method of this invention, hop strains may be reliably identified without any effect from the environment where they were harvested.

This invention will now be described in more detail with reference to specific examples, but it should be understood that the invention is in no way limited to these examples.

BRIEF DESCRIPTION OF THE DRAWINGS

FIG. 2 is a diagram showing a base sequence of amplified fragments subjected to electrophoresis in the vicinity of 600 bp indicated by the arrow in FIG. 1; the upper group shows the base sequence of HT (SEQ ID NO: 43) and the lower group shows the base sequence of SW (SEQ ID NO: 44). Identical bases at positions corresponding to HT in the upper group are shown by a black dot (○), and where there is a base substitution at positions corresponding to both, the base is shown. Positions where there are no bases corresponding to either type, i.e. missing positions, are shown by a minus sign (−).

The frame enclosure labeled B72WF2 contains a base sequence described in SEQ.ID No: 27 of the sequence listing which is selected as an identifying primer. The frame enclosure B72WR2 contains a base sequence described in SEQ.ID No: 28 of the sequence listing which is a complementary sequence of an identifying primer.

Figure 3:
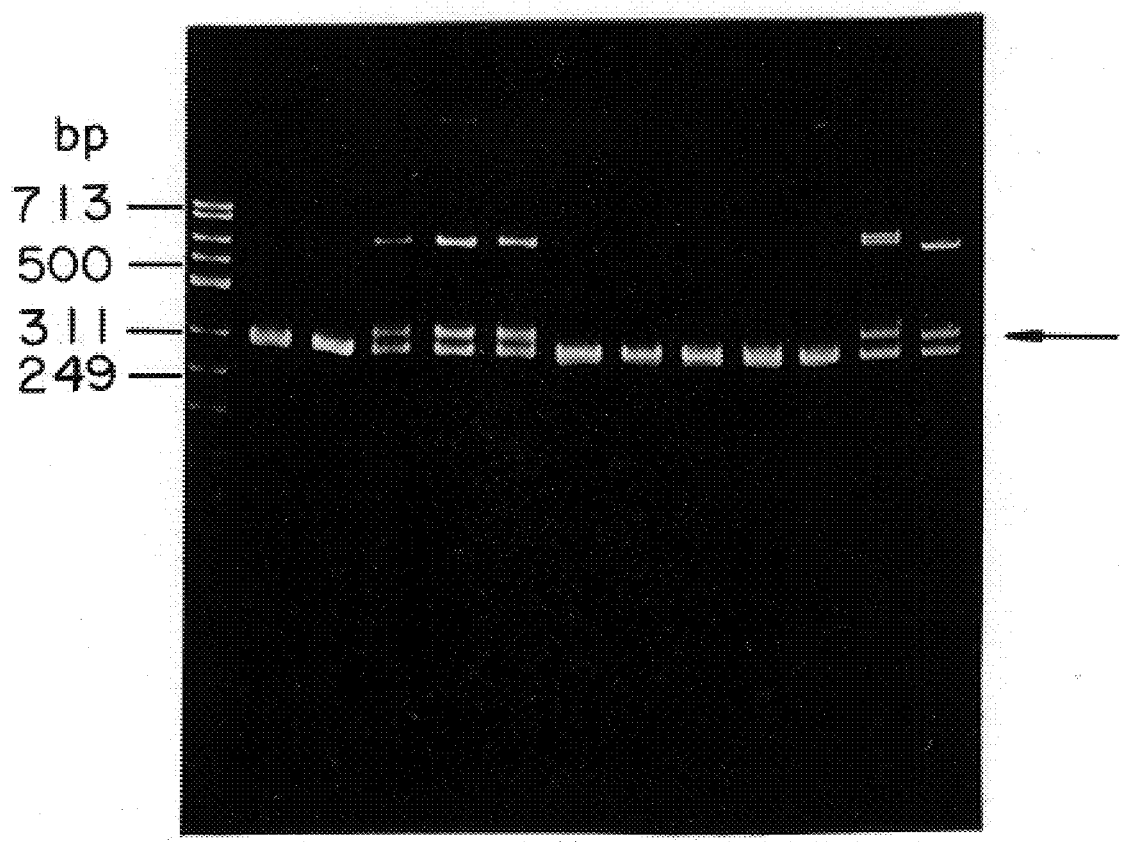

FIG. 3 is a photograph showing the results of electrophoresis to fractionate amplified fragments when PCR is performed using an identifying primer comprising B72WF2 (SEQ.ID No: 27) and the complementary sequence of B72WR2 (SEQ.ID No: 28) shown in FIG. 2.

FIG. 4 is a drawing showing a base sequence of another polymorphic amplified fragment (RAPD marker) (SEQ ID NO:45).

FIG. 5 is a drawing showing a base sequence of yet another polymorphic amplified fragment (RAPD marker) (SEQ ID NO:46).

DETAILED DESCRIPTION OF EMBODIMENT

In the hop strain identifying method according to this invention, polymorphic regions, i.e. portions of DNA where the DNA sequence is different for different hop varieties, are amplified by PCR using an identifying primer, and the strains are identified by analyzing the difference between amplified fragments.

COLLECTION OF HOP DNA

Hop DNA for study may be collected from minute amounts of hop leaves, cones and pellets.

Hop DNA may be collected by any method generally used to recover DNA from plant specimens, for example the typical DNA extraction method given in Nucleic Acids Res., 8, 4321 (1980), or the extraction may be performed more simply using a commercial BLOOD AND CELL CULTURE DNA KIT (QIAGEN Inc.). When the kit is used, the DNA is absorbed in a negative ion exchange resin column and recovered, so problems due to admixture of substances that might interfere with the reactions may be resolved.

Some methods of designing an identifying primer that may be used in this invention will now be described.

FIRST IDENTIFYING PRIMER DESIGN METHOD

To design the primer, any method may be used which searches for oligonucleotide that detect polymorphic regions or sequences in different varieties by PCR, but the RAPD method is particularly convenient.

To perform the RAPD method, a primer group comprising a plurality of primers is first prepared.

The primers used in the ordinary RAPD method may be obtained with a DNA automatic synthesis kit using, for example, the phosphoamidide technique. They have random sequences, and their length is 6–40 mer or more preferably 10–21 mer.

The base sequence disclosed by Williams et al (Nucleic Acids Research, Vol. 18, p.6531, 1990), Beck's common primer or a commercial oligonucleotide from Operon 10-mer Kits made by the OPERON Co. may also be employed. PCR is then performed on the different types of hop DNA using one or more primers from the group prepared above, under the same conditions as those of the "PCR reaction" described hereafter.

Subsequently, the fragments amplified by PCR are fractionated on a suitable electrophoresis gel, and the migration degree of the amplified fragments is compared between strains.

As a result of the above comparison, amplified fragments which are found to be different or found to have a size difference between strains are taken as polymorphism amplifying fragments (RAPD markers), and one or two primers producing these fragments are selected from the above primer group to be used as identifying primers.

Examples of such an identifying primer selected in this way is a synthetic oligonucleotide comprising a base sequence described in SEQ.ID Nos: 1–14 of the sequence listing, and these sequences may of course also be used as complementary sequences.

Any oligonucleotide comprising part of the base sequence shown by SEQ.ID Nos: 1–14 of the sequence listing may be used in the PCR reaction as an identifying primer provided it can amplify any desired polymorphic sequence of hop DNA.

Further, depending on the PCR reaction conditions, any nucleotide comprising a base sequence similar to that of the aforesaid synthetic oligonucleotide may also be used.

This first design method makes it easy to design an identifying primer that can detect polymorphism in hops containing unknown sequences.

Moreover, the identifying primer designed by this method fulfills its function very well as will be shown in the following examples.

SECOND IDENTIFYING PRIMER DESIGN METHOD

The second identifying primer design method determines their base sequence of polymorphic amplified fragments (RAPD marker) detected in the first identifying primer design method and detects polymorphic sequences.

Sequences which can produce amplified fragments containing a polymorphic sequence are selected as the identifying primer from the sequences in the polymorphic amplified fragments determined here.

A primer of the type listed in "PCR technology", ed. Henry A. Erlich, Takara Shuzo Co., Ltd. which is often quoted in PCR, may be designed.

Specifically, when selecting a primer sequence from the DNA amplification fragment shows size variations as a RAPD marker, an oligonucleotide comprising sequences situated on either side of an insertion or deletion in the RAPD marker base sequence is selected.

An example of such an identifying primer is a combination of oligonucleotide comprising the base sequences described in SEQ.ID Nos. 27, 28 of the sequence listing.

The size variation of the RAPD marker is from 1 bp to several hundred bp, but a range of 10 bp to several tens of bp is more convenient for identification. There may also be base substitutions which can be identified by restriction enzymes or the like even if there is no size variation.

The size variation which can easily be distinguished by electrophoresis depends on the type and concentration of gel used, but as a rule it may be 1/10 or more of the total length.

For example, the primer is designed so that when the insertion sequence is 20 bp, the full length of the amplified product is 200 bp or less. Therefore, by using PCR with this type of identifying primer, amplified fragments are obtained which make size variations due to polymorphism easy to distinguish.

Alternatively, when the amplified fragments show size variations between varieties, oligonucleotide may be chosen comprising internal sequences at insertion sites and sequences at positions bridging sites where there are deletions. Therefore, by using PCR with this type of identifying primer, amplified fragments are obtained for varieties having insertions and/or deletions.

When the RAPD marker can identify the presence or absence of specific DNA amplification bands depending on the strain, an oligonucleotide comprising an optimum sequence for the polymerase chain reaction is selected from the internal base sequence of the RAPD marker as primer. An example of such a primer are oligonucleotide comprising the base sequences described in SEQ.ID Nos: 35, 36 of the sequence listing.

Further, when it appears that there is polymorphism only at the position wherein the primary primer anneals, a synthetic oligonucleotide comprising a primary primer sequence at the 5' terminus and comprising 5–20 of the RAPD marker base sequences, may be selected.

For example when a primer comprising internal base sequences of the RAPD marker is used and PCR amplified products of the same size are produced for all varieties, the specificity can be enhanced by designing the primer in this way. As a specific example, a primer comprising the base sequences described in SEQ.ID Nos: 15 and 16 of the sequence listing may also comprise the base sequence described in SEQ.ID No: 12 of the sequence listing at the 5' terminus with base sequences joined to it (FIG. 5). However, when the base sequence in the RAPD marker to be joined is too short, non-specific amplification bands increase in PCR which make detection of polymorphism impossible. On the other hand when it is too long, primers anneal to every strain regardless of the presence or absence of polymorphism so that PCR products are produced and detection of polymorphism is again impossible.

When there are recognition sites for restriction enzymes in the RAPD marker base sequence which would enable identification of varieties so the primer can be designed to obtain PCR amplified products which retain these enzyme recognition sites. Example of such a primer are oligonucleotide comprising the base sequences described in the SEQ.ID Nos: 33, 34 of the sequence listing.

When the primer is designed in this way, the annealing temperature may be set when PCR is performed so that only the target fragment (RAPD marker) are amplified. The identification of DNA amplification bands is therefore easy, and highly reliable results are obtained.

Synthetic oligonucleotide provide a simple means of obtaining the primers designed in the way described above. The synthetic oligonucleotide used in this invention may be obtained using a commercial DNA autosynthesis machine with, for example, the phosphoamidide method.

The chain length of this oligonucleotide is 15–40, but more preferably 20–30. An oligonucleotide comprising any of the base sequences described in SEQ.ID Nos: 1–40 of the sequence listing may conveniently be used.

In addition to the above, a synthetic oligonucleotide may also be used which comprises part of the hop DNA base sequence between positions to which other synthetic oligonucleotide comprising two kinds of base sequences among the base sequences described in SEQ.ID Nos: 15–40 of the sequence listing (e.g. 15 and 16, 17 and 18 . . . 35 and 36, etc.), are complementary.

The identifying primers according to the aforesaid second design method amplify the polymorphic region to permit a suitable identification based on polymorphic amplified fragments, i.e. sequences surrounding the polymorphic. sequences, and also comprise sequences which are suitable for PCR. A precise strain identification can therefore be made using these primers.

PCR REACTION

Next, the polymorphic region in hop DNA is amplified by PCR using identifying primers designed according to the first or second design method above.

The PCR reaction is, for example, disclosed by Saiki et. al, Science, vol. 230, p.1350–1354. Specifically, the reaction comprises the following steps: a step for denaturing template DNA, a step for annealing a primer with template DNA, and a step for performing a DNA replication cycle comprising an extension step by DNA polymerase with the primer as the starting point.

The PCR reaction was performed by treating each strain in a separate reaction tube. The reaction solution was prepared by adding one or two types of synthetic oligonucleotide, DNA polymerase, 4 kinds of deoxyribonucleotides (dATP, dTTP, dCTP, dGTP), DNA of each hop variety as a template DNA, and an amplifying buffer solution (comprising approx. 1.0 $\mu$M to approx. 4.0 $\mu$M but preferably approx. 1.5 $\mu$M to approx. 3.0 $\mu$M of magnesium chloride, potassium chloride, gelatin, bovine serum albumin, a surfactant (e.g. Tween 20, NP-40, Triton X-100 (all commercial names), and dimethylsulfoxide). The reaction tube containing this reaction solution was set in a thermocycler or the like, and the aforesaid DNA replication cycle was performed a suitable number of cicles, e.g. approx. 20 cicles to approx. 50 cicles but preferably approx. 25 cicles to approx. 40 cicles.

The PCR reaction steps may be performed, for example, under the following conditions.

The denaturing step is normally performed by heating from 90° C. to 95° C. but preferably from 94° C. to 95° C., for approx. 1 min to approx. 3 min but preferably for approx. 1 min to approx. 2 min.

The primer annealing step is normally performed by incubating with the primer from 30° C. to 50° C. but preferably from approx. 35° C. to approx. 42° C., for approx. 1 min to approx. 3 min but preferably for approx. 1 min to approx. 2 min. The identifying primer may be one type, or a combination of two or more types, as desired.

The DNA polymerase extension step is performed in the presence of thermostable DNA polymerase, normally from approx. 70° C. to approx. 73° C. but preferably from approx. 72° C. to approx. 73° C., and from approx. 1 min to approx. 4 min but preferably from approx. 2 min to approx. 3 min. This thermostable DNA polymerase may be commercial thermostable DNA polymerase manufactured by PERKIN ELMER Ltd.

The desired amplified DNA may be obtained by repeating the above steps.

ANALYSIS OF AMPLIFIED FRAGMENTS

The amplified DNA produced by the PCR reaction using the aforesaid identifying primers is fractionated by electrophoresis which is the usual method of fractionating DNA. The strains may then be identified based on the migration pattern obtained.

In electrophoresis, a suitable migration pattern may be obtained by using approx. 3% to approx. 20% polyacrylamide gel for DNA fragments of 1000 deoxyribonucleotides pairs or less, and approx. 0.2% to approx. 2% agarose gel for longer DNA fragments.

The buffer solution used for electrophoresis may be a Tris-phosphoric acid system (pH 7.5–8.0), Tris-acetic acid system (pH 7.5–8.0) or a Tris-boric acid system (pH 7.5–8.3), but is preferably a Tris-phosphoric acid system. EDTA may also be added if necessary.

The electrophoresis conditions are different depending on the size of the electrophoresis apparatus, but may, for example, be 50–300V for 10–120 min, and preferably 150 V for 30 min. As a size marker simultaneously subjected to electrophoresis as a comparison, a commercial marker such as 100 Base-Pair Ladder (Pharmacia Inc.) may be used.

The amplified DNA may be visually detected by a substance such as a phenanthridine dye, for example ethidium bromide, which also interacts with nucleic acids. The staining technique is either to first add a substance such as ethidium bromide so as to give a final concentration of approx. 0.5 mg/ml, or to immerse the gel after electrophoresis in an aqueous solution of ethidium bromide containing approx. 0.5 mg/ml for approx. 10 to 60 min. When the stained gel is irradiated by UV light of 254 nm or 366 nm in a dark room, the migration pattern may be detected as red bands where DNA is combined with ethidium bromide. It will be appreciated that when the staining solution is added to the electrophoresis apparatus, this migration pattern may be visually observed even during electrophoresis.

In addition to this electrophoresis method, the amplified DNA may be analyze by any means which can detect its presence or absence, or size.

STRAIN IDENTIFICATION

Strains are identified by a comparative analysis of migration patterns obtained as described above. The comparative analysis may be performed, for example, based on differences in the presence or absence, or differences in the size, of predetermined amplified DNA among varieties.

The presence or absence of amplified DNA in a specific variety shows whether the primer used for PCR comprises an annealed sequence (i.e. complementary sequence), and size differences of amplified DNA show that there are polymorphic sequences such as deletions or insertions in the region amplified by PCR depending on the variety.

To perform a more precise identification of strains, it is preferable not to rely on the result of only one PCR, but to compare migration patterns of amplified fragments when one or two different oligonucleotide are used as identifying primers.

Moreover, the precision with which varieties can be identified and the capacity to distinguish between them may be improved by observing the results obtained when the conditions of the PCR are varied, e.g. annealing temperature, magnesium concentration in the reaction buffer solution, etc.

The hop strain identifying method according to this invention, by performing the above sequence of operations, can clearly distinguish different varieties.

APPLICATIONS

The variety identifying method of this invention can be applied to verify the purity of hop varieties used for hop products such as hop pellets.

For example, a study is made of the difference between the amplified DNA obtained from standard hops and the amplified DNA obtained from hop pellets. If amplified DNA is detected apart from that obtained from the standard hops, it may be determined that other varieties or species are mixed with the standard hops in the pellets.

When other varieties or species are expected to be present, the amount of amplified DNA, the extent to which these other varieties or species are present, i.e. the purity, may be measured by observing, for example, the intensity of the coloration due to ethidium bromide described above.

In this case also, the precision of the purity assessment may be enhanced by using two or more of the synthetic oligonucleotide according to this invention in conjunction.

It may be expected that the oligonucleotide of this invention may be applied to the identification of species in plants other than hops (e.g. mulberries, strawberries, cherries, etc.). Positions where the deoxyribonucleotides sequence is different in close species are positions where DNA mutations occur easily, and they are therefore limited. For example, it is reported that the position for coding rDNA may be used to identify species of bacteria (*E. coli*, lactic acid bacteria) or plants (rice seedlings, oranges). Therefore, positions where a difference was found between close species according to this invention may probably also be used to identify strains in another plant.

The variety identifying method according to this invention performs an analysis based on polymorphism of sequences among varieties, and can therefore make an accurate distinction between hop varieties unaffected by environmental factors. Further, the variety identifying method according to this invention may be used not only for identifying varieties, but also for measuring the purity of different hop varieties in hop products.

EMBODIMENT

1–12 show a hop strain identification using an identifying primer designed by the first identifying primer design method.

EXAMPLE 1
Extraction of genome DNA

The hops used were Brewer's Gold (referred to hereafter as strain No. 1), Northern Brewer (referred to hereafter as strain No. 2), Tettnanger (referred to hereafter as strain No. 3), Saazer (referred to hereafter as strain No. 4), Hersbrucker spaet (referred to hereafter as strain No. 5), Spalter select (referred to hereafter as strain No. 6), Hallertauer tradition (referred to hereafter as strain No. 7), Shinshu Wase (referred to hereafter as strain No. 8) and Furano Ace (referred to hereafter as strain No. 9).

Green leaf tissue (raw weight Ig) from the above varieties was finely chopped, and the tissue fragments frozen by immersing in liquid nitrogen. After converting the frozen substance to a powder in liquid nitrogen using a Polytron, genome DNA was extracted from 50 mg of the powder using a BLOOD AND CELL CULTURE DNA KIT (QIAGEN Inc.). 10–20 mg of genome DNA was finally obtained for each variety.

EXAMPLE 2

Classification of hop varieties was performed by PCR with oligonucleotide described in SEQ. ID Nos: 1 and 2 as primer. A polymerase chain reaction was performed in microtube containing 50 $\mu$M KCl, 1.5 $\mu$M MgCl$_2$ and 10 $\mu$M Tris-HCl buffer solution (pH 8.8) containing 0.1% Triton X-100. To the tube were added one unit of thermostable DNA polymerase (Wako Pure Chemicals), 20 nanomoles of four bases (dATP, dTTP, dCTP, dGTP) and 0.1 mg of each hop variety genome DNA prepared in Example 1, 33 picomoles of the oligonucleotide described in SEQ.ID Nos: 1 and 2 as primer. The final amount of reaction solution was 30 ml and approx. 20 ml of mineral oil was added to the tube to prevent evaporation of the reaction solution.

The above polymerase chain reaction was performed under the following conditions. First, after maintaining the temperature at 94° C. for 3 min, a denaturing step was performed by heating at 94° C. for 1 min, and a primer annealing step was performed by incubating at 35° C. for 1 min. A DNA polymerase extension step was performed by carrying out 35 treatment cycles with thermostable DNA polymerase at 72° C. for 2 min each, and maintaining the temperature at 72° C. for 10 min. The product was stored at 4° C.

The amplified DNA obtained by the above polymerase chain reaction was separated by electrophoresis at 150 V for 30 min in 100 $\mu$M Tris-boric acid buffer solution (pH. 8.0) containing 2 $\mu$M EDTA using 5% polyacrylamide gel. 100 Base-Pair Ladder (Pharmacia Inc.) was used as a size marker.

After electrophoresis, the gel was immersed in a 0.5 mg/ml aqueous solution of ethidium bromide for 10 min, and irradiated in a dark room with UV at 254 nm. A red band was detected corresponding to a compound of DNA with ethidium bromide. The results obtained are shown in Table 1.

As is clear from the table, when synthetic oligonucleotide comprising the deoxyribonucleotides sequences described in SEQ.ID Nos: 1 and 2 were used as primer, two amplified genome bands were detected at approx. 520 bp and approx. 530 bp. From the presence or absence of these bands, nine hop varieties were classified into two categories.

| | SEQ. ID Nos. | | | | | | |
|---|---|---|---|---|---|---|---|
| | 1, 2 | | 3, 4 | 5, 6 | 7, 8 | | 9 |
| | Amplified DNA (bp) | | | | | | |
| Hop strain no. | 520 | 530 | 750 | 850 | 270 | 370 | 950 | 1200 |
| 1 | | ○ | | ○ | ○ | | ○ | |
| 2 | | ○ | | ○ | | | | |
| 3 | | ○ | ○ | | | | | ○ |
| 4 | | ○ | ○ | | | | | ○ |
| 5 | | ○ | ○ | ○ | | ○ | | |
| 6 | | ○ | | ○ | | | | |
| 7 | | ○ | | | | | | |
| 8 | ○ | | | | ○ | ○ | ○ | |
| 9 | | ○ | ○ | ○ | ○ | | ○ | |

EXAMPLE 3

The method was identical to that of Example 2 except that synthetic oligonucleotide described in SEQ.ID Nos: 3 and 4 were used as primer, and the primer annealing step in the polymerase chain reaction was performed at 40° C. The results are shown in Table 1.

When synthetic oligonucleotide described in SEQ.ID Nos: 3 and 4 were used as primer, two amplified genome bands were detected at approx. 750 bp and approx. 850 bp. From the presence or absence of these bands, nine hop varieties were classified into four categories.

EXAMPLE 4

The method was identical to that of Example 2 except that synthetic oligonucleotide described in SEQ.ID Nos: 5 and 6 were used as primer, and the primer annealing step in the polymerase chain reaction was performed at 40° C. The results are shown in Table 1.

When synthetic oligonucleotide described in SEQ.ID Nos: 5 and 6 were used as primer, one amplified genome band was detected at approx. 270 bp. From the presence or absence of this band, nine hop varieties were classified into two categories.

EXAMPLE 5

The method was identical to that of Example 2 except that synthetic oligonucleotide described in SEQ.ID Nos: 7 and 8 were used as primer.

When synthetic oligonucleotide described in SEQ.ID Nos: 7 and 8 were used as primer, one amplified genome band was detected at approx. 370 bp. From the presence or absence of this band, nine hop varieties were classified into two categories.

EXAMPLE 6

The method was identical to that of Example 2 except that a synthetic oligonucleotide described in SEQ.ID No: 9 was used as primer, and the primer annealing step in the polymerase chain reaction was performed at 40° C. The results are shown in Table 1.

When a synthetic oligonucleotide described in SEQ. ID No: 9 was used as primer, two ampiified genome bands were detected at approx. 950 bp and approx. 1200 bp. From the presence or absence of these bands, nine hop varieties were classified into three categories.

EXAMPLE 7

The method was identical to that of Example 2 except that a synthetic oligonucleotide described in SEQ.ID No: 10 was used as primer, and the primer annealing step in the polymerase chain reaction was performed at 38° C. The results are shown in Table 2.

When a synthetic oligonucleotide described in SEQ.ID No: 10 was used as primer, three amplified genome bands were detected at approx. 650 bp, approx. 700 bp and approx. 1200 bp. From the presence or absence of these bands, nine hop varieties were classified into four categories.

TABLE 2

| | Hop strain no. | | | | | |
|---|---|---|---|---|---|---|
| | 10 | | 11 | | 12 | |
| | Amplified DNA (bp) | | | | | |
| SEQ. ID Nos. | 650 | 700 | 1200 | 1400 | 550 | 800 |
| 1 | | | ○ | ○ | ○ | ○ |
| 2 | ○ | | ○ | | | |
| 3 | ○ | | ○ | | | |
| 4 | | | ○ | | | |
| 5 | | | ○ | | | |
| 6 | | | ○ | | | |
| 7 | | | ○ | | | ○ |
| 8 | ○ | ○ | ○ | ○ | ○ | |
| 9 | | ○ | | ○ | ○ | |

EXAMPLE 8

The method was identical to that of Example 2 except that a synthetic oligonucleotide described in SEQ.ID No: 11 was used as primer, and the primer annealing step in the polymerase chain reaction was performed at 38° C. The results are shown in Table 1.

When a synthetic oligonucleotide described in SEQ.ID No: 11 was used as primer, one amplified genome band was detected at approx. 1400 bp and approx. 1200 bp. From the presence or absence of these bands, nine hop varieties were classified into two categories.

EXAMPLE 9

The method was identical to that of Example 2 except that a synthetic oligonucleotide described in SEQ.ID No: 12 was used as primer, and the primer annealing step in the polymerase chain reaction was performed at 38° C. The results are shown in Table 2.

When a synthetic oligonucleotide described in SEQ.ID No: 12 was used as primer, two amplified genome bands were detected at approx. 550 bp, and approx. 800 bp. From the presence or absence of these bands, nine hop varieties were classified into four categories.

EXAMPLE 10

The method was identical to that of Example 2 except that a synthetic oligonucleotide described in SEQ.ID No: 13 was used as primer, and the primer annealing step in the polymerase chain reaction was performed at 38° C. The results are shown in Table 3.

When a synthetic oligonucleotide described in SEQ.ID No: 13 was used as primer, four amplified genome bands were detected at approx. 500 bp, 640 bp, 650 bp and 140 bp. From the presence or absence of these bands, nine hop varieties were classified into five categories.

TABLE 3

| | SEQ. ID Nos. | | | | |
|---|---|---|---|---|---|
| | 13 | | | | 14 |
| | Amplified DNA (bp) | | | | |
| Hop strain no. | 500 | 640 | 650 | 1400 | 540 |
| 1 | ○ | | ○ | ○ | ○ |
| 2 | ○ | | ○ | | ○ |
| 3 | | | ○ | | ○ |
| 4 | | | ○ | | |
| 5 | | | ○ | ○ | |
| 6 | | | ○ | ○ | |
| 7 | ○ | | ○ | | ○ |
| 8 | | ○ | | ○ | ○ |
| 9 | ○ | | ○ | ○ | |

EXAMPLE 11

The method was identical to that of Example 2 except that a synthetic oligonucleotide described in SEQ.ID NO: 14 was used as primer, and the primer annealing step in the polymerase chain reaction was performed at 38° C. The results are shown in Table 3.

When a synthetic oligonucleotide described in SEQ.ID No: 14 was used as primer, one amplified genome band was detected at approx. 540 bp. From the presence or absence of these bands, nine hop varieties were classified into two categories.

EXAMPLE 12

Hop pellets sold as strain no. 8 (manufactured by the Northern Hop Agricultural Cooperative, Iwate-ken under license from Sapporo Breweries Ltd.) were crushed in a mortar to a powder and from 20 mg of the powder and approx. 5 mg of genome DNA was extracted using BLOOD AND CELL CULTURE DNA KIT (QIAGEN Inc.). The same procedure was applied to this DNA as that of Example 2 using synthetic oligonucleotide comprising the deoxyribonucleotides sequences described in SEQ.ID Nos. 1 and 2 as primer.

The difference between the detected amplified genome DNA and the amplified genome DNA obtained from standard hops of variety no. 8 was examined to verify purity.

Next, a hop strain identification using an identifying primer designed according to the second identifying primer design method will be described in Examples 13–30.

EXAMPLE 13

Extraction of genome DNA

Green leaf tissue (raw weight 1 g) from the above varieties was finely chopped, and the tissue fragments frozen by immersing in liquid nitrogen. After converting the frozen substance to a powder in liquid nitrogen using a Polytron, genome DNA was extracted from 50 mg of the powder using a BLOOD AND CELL CULTURE DNA KIT (QIAGEN Inc.). 10–20mg of genome DNA was finally obtained for each variety.

EXAMPLE 14

Selection of RAPD marker

For obtaining RAPD marker, PCR was performed with 0.34 $\mu$M of primer-B72 (FIG. 2) as primer.

A polymerase chain reaction was performed in a microtube containing 50CM KCl, 1.5 $\mu$M MgCl$_2$ and 10 $\mu$M Tris-HCI buffer solution (pH 8.8) containing 0.1% Triton X-100. To the microbe tube were added 0.25 units of Taq DNA polymerase (Nippon Gene K. K.), 200 $\mu$M each of four bases (DATP, dTTP, dCTP, dGTP) and 17.5 ng of each hop variety genome DNA prepared in Example 13. The final amount of reaction solution was 10 ml.

The above polymerase chain reaction was performed under the following conditions. First, after maintaining the temperature at 94° C. for 1 min, a denaturing step was performed by heating at 94° C. for 30 seconds, and a primer annealing step was performed by incubating at 33° C. for 1 min. A DNA polymerase extension step was performed by carrying out 35 treatment cycles with thermostable DNA polymerase at 72° C. for 30 seconds each, and maintaining the temperature at 72° C. for 1 min.

The amplified DNA obtained by the above polymerase chain reaction was separated by electrophoresis at 150 V for 30 min in 100 $\mu$M Tris-boric acid buffer solution (pH. 8.0) containing 2 $\mu$M EDTA using 5% polyacrylamide gel. Marker 9 (Nippon Gene) was used as a size marker.

After electrophoresis, the gel was immersed in a 0.5 mg/ml aqueous solution of ethidium bromide for 10 min, and irradiated in a dark room with UV at 254 nm. A red band was detected corresponding to a compound of DNA with ethidium bromide. The results obtained are shown in FIG. 1.

Figure 1:
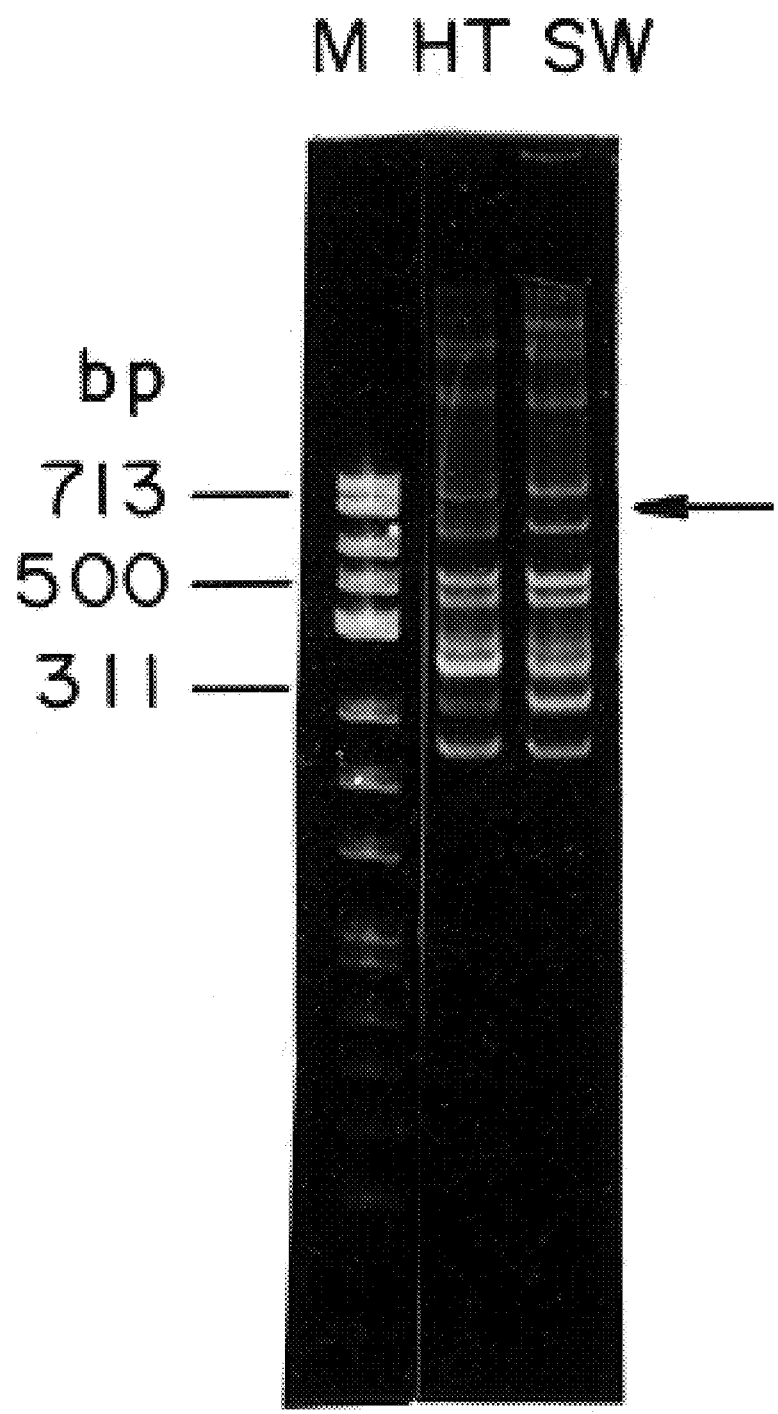
FIG. 1 is a photograph showing a migration pattern obtained when part of the DNA of Hallertauer Tradition (HT) and Shinshu Wase (SW) were respectively amplified using a primary primer (one type of primer: B72), and the amplified fragments were subjected to electrophoresis according to the second identifying primer design method.

From FIG. 1, it is seen that the size of the bands in the positions shown by the arrow is different for HT and SW. The position of the band shown by the arrow corresponds to the RAPD marker.

EXAMPLE 15

The RAPD marker prepared in Example 14 was cut out from the electrophoresis gel, introduced into a dialysis tube, subjected to a voltage and eluted from the gel.

Recognition sequences of the restriction enzyme BglII or PstI were added to the RAPD marker obtained according to the method described in "PCR Technology" (ed. Henry A. Erlich, pub. Takara Shuzo Co., Ltd.). After sub-cloning with the pUC plasmid using this restriction enzyme recognition sequence, the deoxyribonucleotides sequence was determined by the dideoxy method and is shown in FIG. 2. In the figure, the dot symbol (o) shows the same deoxyribonucleotides as in the upper row, and the bar (-) shows a missing base. The underlined part is the deoxyribonucleotides sequence of the primer B72, and the deoxyribonucleotides sequence enclosed by the rectangle is a deoxyribonucleotides sequence to which reference is made in Example 16 hereafter.

When sequencing was performed for each band, the insertion of a 32 bp deoxyribonucleotides sequence was observed in SW as shown in FIG. 2.

EXAMPLE 16

Of the RAPD markers obtained in Example 15, a synthetic oligonucleotide described in SEQ.ID 27 of the sequence listing obtained by referring to the deoxyribonucleotides sequence B72WF2 enclosed by a rectangle shown in FIG. 2, and the deoxyribonucleotides sequence described in SEQ.ID 28 obtained from the complementary sequence B72WR2 were designed (production subcontracted to Sawaddy Technology).

These synthetic oligonucleotides were used in the following PCR reaction as a primer set. RCR was performed in the 10 ml of reaction solution containing 50 $\mu$M MgCl$_2$ and 10 $\mu$M Tris-HCI buffer solution (pH 8.8) containing 0.1% Triton X-100, to 0.25 units of Taq DNA polymerase (Nippon Gene Inc.), 200 mm of the four bases (dATP, dTTP, dCTP, dGTP), 17.5 ng of the genome DNA of each hop strain prepared in Example 13 and 0.34 $\mu$M of the synthetic oligonucleotides.

The steps in the above PCR were performed under the following conditions. First, after maintaining the temperature at 94° C. for 1 min, a denaturing step was performed by heating at 94° C. for 1 min, and a primer annealing step was performed by incubating at 60° C. for 1 min. A DNA polymerase extension step was performed by carrying out 35 treatment cycles with thermostable DNA polymerase at 72° C. for 30 seconds each.

The amplified DNA obtained by the above polymerase chain reaction was separated by electrophoresis at 150 V for 30 min in 100 $\mu$M Tris-boric acid buffer solution (pH. 8.0) containing 2 $\mu$M EDTA using 5% polyacrylamide gel. Marker 9 (Nippon Gene) was used as a size marker.

After electrophoresis, the gel was immersed in a 0.5 mg/ml aqueous solution of ethidium bromide for 10 min, and irradiated in a dark room with UV at 254 nm. A red band was detected corresponding to a compound of DNA with ethidium bromide. The results obtained are shown in FIG. 3.

The same procedure was performed for other varieties, and the results are shown in FIG. 3. The other strains used were Fuggle (FU), Cascade (CC), Brewer's Gold (BG), Northern Brewer (NB), Tettnanger (TE), Saazer (SA), Hersbrucker spaet (HE), Perle (PE), Spatter select (SS) and Furano Ace (FA).

As can be seen from the figure, amplification of a 329 bp fragment (arrow) comprising the insertion position was observed for BG, NB, TE, SW and FA. A 299 bp fragment not comprising the insertion position was observed for all strains. The strain-specific fragments 600 bp, 700 bp, 710 bp were also observed. These fragments are easy to identify and were observed with high reproducibility.

EXAMPLE 17

The method was identical to that of Example 16 except that synthetic oligonucleotides described in SEQ.ID Nos: 15 and 16 were used as primer. The results are shown in Table 4.

From the table, it is seen that when the synthetic oligonucleotides described in SEQ.ID Nos: 15 and 16 were used as primer, one amplified genome band was detected at approx. 500 bp. From the presence or absence of this band, twelve hop varieties were classified into two categories.

EXAMPLE 18

The method was identical to that of Example 16 except that synthetic oligonucleotides described in SEQ.ID Nos: 17 and 18 were used as primer, and the primer annealing step in PCR was performed at 62° C. The results are shown in Table 4.

When synthetic oligonucleotides described in SEQ.ID Nos: 17 and 18 were used as primer, one amplified genome band was detected at approx. 260 bp. From the presence or absence of this band, twelve hop varieties were classified into two categories.

EXAMPLE 19

The method was identical to that of Example 16 except that synthetic oligonucleotides described in SEQ.ID Nos: 19 and 20 were used as primer, and the primer annealing step in PCR was performed at 65° C. The results are shown in Table 4.

When synthetic oligonucleotides described in SEQ.ID Nos: 19 and 20 were used as primer, two amplified genome bands were detected at approx. 500 bp and approx. 550 bp. From the presence or absence of these bands, twelve hop varieties were classified into two categories.

EXAMPLE 20

The method was identical to that of Example 16 except that synthetic oligonucleotides described in SEQ.ID Nos: 21 and 22 were used as primer. The results are shown in Table 4.

When synthetic oligonucleotides described in SEQ.ID Nos: 21 and 22 were used as primer, one amplified genome band was detected at approx. 710 bp. From the presence or absence of this band, twelve hop varieties were classified into two categories.

EXAMPLE 21

The method was identical to that of Example 16 except that synthetic oligonucleotides described in SEQ.ID Nos: 23 and 24 were used as primer. The results are shown in Table 4.

When synthetic oligonucleotides described in SEQ.ID Nos: 23 and 24 were used as primer, one amplified genome band was detected at approx. 330 bp. From the presence or absence of this band, twelve hop varieties were classified into two categories.

EXAMPLE 22

The method was identical to that of Example 16 except that synthetic oligonucleotides described in SEQ.ID Nos: 25 and 26 were used as primer, and after performing PCR, 20 PCR cycles were performed under the same conditions as those of the previous PCR using 1 ml of reaction solution as a template DNA. The results are shown in Table 4.

When synthetic oligonucleotides described in SEQ.ID Nos: 25 and 26 were used as primer, two amplified genome bands were detected at approx. 160 bp and approx. 200 bp. From the presence or absence of these bands, twelve hop varieties were classified into two categories.

EXAMPLE 23

The method was identical to that of Example 16 except that synthetic oligonucleotides described in SEQ.ID Nos: 29 and 30 were used as primer, and the primer annealing step in PCR was performed at 57° C. The results are shown in Table 4.

When synthetic oligonucleotides described in SEQ.ID Nos: 29 and 30 were used as primer, one amplified genome band was detected at approx. 350 bp. From the presence or absence of this band, twelve hop varieties were classified into two categories.

EXAMPLE 24

The method was identical to that of Example 22 except that synthetic oligonucleotides comprising the deoxyribonucleotides sequences described in SEQ.ID Nos: 30 and 31 were used as primer, PCR was performed twice, and the reaction solution was treated with the restriction enzyme NlaIII (Daiichi Pure Chemicals). The results are shown in Table 4.

When synthetic oligonucleotides comprising the deoxyribonucleotides sequences described in SEQ.ID Nos: 31 and 32 were used as primer, two amplified genome bands were detected at approx. 220 bp and approx. 360 bp. From the presence or absence of these bands, twelve hop varieties were classified into four categories.

EXAMPLE 25

The method was identical to that of Example 16 except that synthetic oligonucleotides described in SEQ.ID Nos: 33 and 34 were used as primer, the primer annealing step in PCR was performed at 67° C., and the reaction solution was treated by the restriction enzyme Taq I (Boehringer Mannheim). The results are shown in Table 4.

When synthetic oligonucleotides described in SEQ.ID Nos: 33 and 34 were used as primer, two amplified genome bands were detected at approx. 220 bp and approx. 270 bp. From the presence or absence of these bands, twelve hop varieties were classified into three categories.

EXAMPLE 26

The method was identical to that of Example 16 except that synthetic oligonucleotides described in SEQ.ID Nos: 35 and 36 were used as primer, and the primer annealing step in PCR was performed at 58° C. The results are shown in Table 4.

When synthetic oligonucleotides described in SEQ.ID Nos: 35 and 36 were used as primer, one amplified genome band was detected at approx. 400 bp. From the presence or absence of this band, twelve hop varieties were classified into two categories.

EXAMPLE 27

PCR and electrophoresis were performed in the same way as in Example 14 using 33 picomoles of Beck's common primer (A25; 5'-GGTCAGGCACCA-3'(SEQ ID NO:47)). As a result, more than ten amplified genome bands were observed from approx. 200 to 2000 bp, and the band at approx. 500 bp which was present or absent depending on the strain, was used as a RAPD marker. When the deoxyribonucleotides sequence of this marker was examined, the results shown in FIG. 4 were obtained.

Synthetic oligonucleotides described in SEQ.ID Nos: 19 and 20 were according to the sequences denoted by A and B enclosed by a rectangle in FIG. 4. Oligonucleotides described in SEQ.ID Nos: 37 and 38 were designed according to the sequences denoted by C and D which are underlined in FIG. 4. These oligonucleotides described in SEQ. ID Nos:37 and 38 comprise parts of the RAPD marker. These oligonucleotides described in SEQ ID Nos: 19 and 20 contain primary sequences at 5'terminus.

The procedure was identical to that of Example 16 except that 35 annealing step cycles at 65° C. were performed for using SEQ ID Nos: 19 and 20 as primer, and 30 annealing step cycles at 60° C. were performed for using SEQ ID Nos: 37 and 38 as primer. As a result when SEQ ID Nos: 19 and 20 were used as primer, bands at 500 bp and 550 bp were observed as shown in Table 4, and when SEQ ID Nos: 37 and 38 were used as primer, a band at 459 bp was observed. From the presence or absence of these bands, twelve hop varieties were classified into two categories.

EXAMPLE 28

PCR and electrophoresis were performed in the same way as in Example 14 using 33 picomoles of Beck's common primer (C16; 5'-CGCCCTGCAGTA-3'(SEQ ID NO:48)). As a result, more than ten amplified genome bands were observed from approx. 200 to 2000 bp, and the band at approx. 500 bp which was present or absent depending on the variety, was used as a RAPD marker. When the deoxyribonucleotides sequence of this marker was examined, the results shown in FIG. 5 were obtained.

Synthetic oligonucleotides described in SEQ.ID Nos: 15 and 16 were based on the sequences denoted by A and B enclosed by a rectangle in FIG. 4. Oligonucleotides described in SEQ.ID Nos: 39 and 40 are based on the sequences C and D which are underlined in FIG. 5.

SEQ. ID Nos: 39 and 40 were used as primer and anealing step were performed at 60° C., 30 cicle. An am amplified genome band at 500 bp was observed for all varieties but the varieties could not be identified. On the other hand when an identical procedure was followed using 15 and 16, the amplified genome bands shown in Table 4 were obtained, and from the presence or absence of these bands, twelve hop strains were classified into two categories.

EXAMPLE 29

From a general overview of Table 4 which summarizes the types in Examples 16–28, it is seen that it is possible to distinguish each of 12 variety of hops.

Examples where the fragment size is listed were taken as a reference for variety identification, and examples where treatment by restriction enzymes was performed are shown in brackets ().

TABLE 4

| Primer set SEQ. ID No. | (bp) | FU | CC | BG | NB | TE | SA | HE | PE | SS | HT | SW | FA |
|---|---|---|---|---|---|---|---|---|---|---|---|---|---|
| 15/16 | 500 | ○ |  | ○ |  |  |  |  |  |  | ○ |  | ○ |
| 17/18 | 260 | ○ | ○ |  | ○ | ○ | ○ | ○ | ○ | ○ | ○ | ○ |  |
| 19/20 | 500 |  |  | ○ | ○ | ○ | ○ |  |  |  | ○ | ○ | ○ |
| 19/20 | 550 |  |  | ○ | ○ | ○ | ○ |  |  |  | ○ | ○ | ○ |
| 21/22 | 710 |  |  |  |  | ○ |  |  |  |  | ○ |  |  |
| 23/24 | 330 |  |  |  | ○ |  |  |  |  |  | ○ |  |  |
| 25/26 | 200 | ○ | ○ | ○ | ○ | ○ | ○ | ○ | ○ | ○ | ○ |  | ○ |
| 25/26 | 160 | ○ |  |  | ○ | ○ |  |  |  | ○ | ○ |  |  |
| 27/28 | 710 |  |  |  |  |  |  |  |  |  | ○ |  |  |
| 27/28 | 700 |  |  |  |  |  |  |  |  |  | ○ |  |  |
| 27/28 | 600 |  |  |  | ○ | ○ | ○ |  |  |  |  |  | ○ |
| 27/28 | 329 |  |  |  | ○ | ○ | ○ |  |  |  |  | ○ | ○ |
| 27/28 | 299 | ○ | ○ | ○ | ○ | ○ | ○ | ○ | ○ | ○ | ○ | ○ | ○ |
| 29/30 | 350 | ○ | ○ |  | ○ | ○ | ○ |  | ○ | ○ | ○ |  | ○ |
| 31/32 | 360(NlaIII) | ○ | ○ |  |  |  | ○ |  | ○ | ○ | ○ | ○ |  |
| 31/32 | 220(NlaIII) | ○ | ○ |  | ○ | ○ |  | ○ |  |  |  | ○ | ○ |
| 33/34 | 270(TaqI) | ○ | ○ | ○ |  | ○ |  |  | ○ |  |  |  | ○ |
| 33/34 | 220(TaqI) |  |  | ○ | ○ | ○ | ○ | ○ | ○ | ○ | ○ | ○ |  |
| 35/36 | 400 |  | ○ |  |  |  |  |  |  |  |  |  |  |
| 37/43 | 459 |  |  | ○ | ○ | ○ | ○ |  |  |  | ○ | ○ | ○ |
| 39/40 | 500 | ○ | ○ | ○ | ○ | ○ | ○ | ○ | ○ | ○ | ○ | ○ | ○ |

EXAMPLE 30

Shinshu Wase hop pellets (manufactured by the Northern Hop Agricultural Cooperative, Iwate-ken under license from Sapporo Breweries Ltd.) were crushed in a mortar, and approx. 5 mg of genome DNA was extracted from 20 mg of the powder using BLOOD AND CELL CULTURE DNA KIT (QIAGEN Inc.). The purity of the DNA obtained was examined by the same procedure as that of Example 29 using synthetic oligonucleotides comprising the deoxyribonucleotides sequences described in SEQ.ID Nos. 15–40 as primer.

Few non-specific amplified bands appeared, and the desired marker could easily be verified. Highly reproducible results were also obtained in repeated purity tests.

FIELD OF APPLICATION

According to the genetic identifying method of this invention, a precise and simple identification of hop varieties which is unaffected by environmental or other conditions, may be made. The genetic identifying method of this invention may also be effectively used to examine the purity of products in which hops are a raw material.

Hence, by identifying hop varieties, the genetic identifying method of this invention may be used to maintain the quality of products containing hops at a constant level, or to improve that quality.

What is claimed is:

1. A random amplified polymorphic DNA (RAPD) method for identifying a variety of the hop plant *Humulus lupulus* comprising:
   (a) providing a variety of the hop plant *Humulus lupulus* and a primer;
   (b) isolating DNA from the variety;
   (c) conducting a polymerase chain reaction using the DNA and the primer;
   (d) determining whether or not the polymerase chain reaction resulted in the production of a DNA molecule; and
   (e) identifying the variety if the DNA molecule was produced, or identifying the variety if the DNA molecule was not produced.

2. The method of claim 1, wherein a plurality of primers is provided, and the polymerase chain reaction is conducted using the plurality of primers.

3. The method of claim 1, wherein the primer is a synthetic oligonucleotide.

4. The method of claim 1,
   wherein the primer comprises a first nucleotide sequence selected from the group consisting of SEQ ID NO:1 to SEQ ID NO:40, or
   the primer comprises a second nucleotide sequence comprising the complement of the first nucleotide sequence.

5. The method of claim 1,
   wherein the primer comprises a first nucleotide sequence selected from the group consisting of SEQ ID NO:1 to SEQ ID NO:14, or
   the primer comprises a second nucleotide sequence comprising the complement of the first nucleotide sequence.

6. The method of claim 1,
   wherein the primer comprises a first nucleotide sequence selected from the group consisting of SEQ ID NO: 15 to SEQ ID NO:40, or
   the primer comprises a second nucleotide sequence comprising the complement of the first nucleotide sequence.

7. A random amplified polymorphic DNA (RAPD) method for constructing a primer for use in identifying a variety of the hop plant *Humulus lupulus* comprising:
   (a) providing a variety of the hop plant *Humulus lupulus* and a first primer;
   (b) isolating DNA from the variety;
   (c) conducting a polymerase chain reaction using the DNA and the first primer, thereby producing a DNA molecule;
   (d) determining the sequence of the DNA molecule;
   (e) constructing a second primer comprising a sequence contained in the DNA molecule, thereby constructing the primer for use in identifying a hop variety.

8. The method of claim 7, wherein a plurality of first primers is provided, and the polymerase chain reaction is conducted using the plurality of first primers.

9. The method of claim 7, wherein the first primer is a synthetic oligonucleotide.

10. The method of claim 6, wherein the second primer is a synthetic oligonucleotide.

11. The method of claim 7,
wherein the first primer comprises a first nucleotide sequence selected from the group consisting of SEQ ID NO:1 to SEQ ID NO:14, or
the first primer comprises a second nucleotide sequence comprising the complement of the first nucleotide sequence.

12. The method of claim 7,
wherein the second primer comprises a third nucleotide sequence selected from the group consisting of SEQ ID NO: 15 to SEQ ID NO:40, or
the second primer comprises a fourth nucleotide sequence comprising the complement of the third nucleotide sequence.

13. The method of claim 7, wherein the second primer comprises a sequence contained in the first primer.

* * * * *

SEQUENCE LISTING (1) GENERAL INFORMATION:

(iii) NUMBER OF SEQUENCES: 48

(2) INFORMATION FOR SEQ ID NO:1:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "SYNTHETIC DNA"

(xi) SEQUENCE DESCRIPTION: SEQ ID NO:1:

CTATTCTGGC TAGTTCTGC                                                    19

(2) INFORMATION FOR SEQ ID NO:2:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "SYNTHETIC DNA"

(xi) SEQUENCE DESCRIPTION: SEQ ID NO:2:

CTATTTTGGC CAGTTTTGT                                                    19

(2) INFORMATION FOR SEQ ID NO:3:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "SYNTHETIC DNA"

(xi) SEQUENCE DESCRIPTION: SEQ ID NO:3:

AGCTGAGCAA GCTTCTTTGG                                               20

(2) INFORMATION FOR SEQ ID NO:4:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "SYNTHETIC DNA"

(xi) SEQUENCE DESCRIPTION: SEQ ID NO:4:

CCCTTTATAT ACACTGCCGA                                               20

(2) INFORMATION FOR SEQ ID NO:5:

(i) SEQUENCE CHARACTERISTICS:
      (A) LENGTH: 20 base pairs
      (B) TYPE: nucleic acid
      (C) STRANDEDNESS: single
      (D) TOPOLOGY: linear

```
        (ii) MOLECULE TYPE: other nucleic acid
             (A) DESCRIPTION: /desc = "SYNTHETIC DNA"

(xi) SEQUENCE DESCRIPTION: SEQ ID NO:5:

TAGCATCGGT AATCTCTCGC                                                   20

(2) INFORMATION FOR SEQ ID NO:6:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "SYNTHETIC DNA"

(xi) SEQUENCE DESCRIPTION: SEQ ID NO:6:

AACATGCTGG GCAACTCCCA                                                   20

(2) INFORMATION FOR SEQ ID NO:7:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "SYNTHETIC DNA"

(xi) SEQUENCE DESCRIPTION: SEQ ID NO:7:

GGAGACATCA TCGAATCAGA                                                   20

(2) INFORMATION FOR SEQ ID NO:8:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "SYNTHETIC DNA"

(xi) SEQUENCE DESCRIPTION: SEQ ID NO:8:

AACCAGAGCA GCCATGTTAG T                                                 21

(2) INFORMATION FOR SEQ ID NO:9:

(i) SEQUENCE CHARACTERISTICS:
             (A) LENGTH: 12 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "SYNTHETIC DNA"

(xi) SEQUENCE DESCRIPTION: SEQ ID NO:9:

GCCAGCTGTA CG                                                           12

(2) INFORMATION FOR SEQ ID NO:10:

(i) SEQUENCE CHARACTERISTICS:
             (A) LENGTH: 19 base pairs
             (B) TYPE: nucleic acid
             (C) STRANDEDNESS: single
             (D) TOPOLOGY: linear
```

(ii) MOLECULE TYPE: other nucleic acid
        (A) DESCRIPTION: /desc = "SYNTHETIC DNA"

(xi) SEQUENCE DESCRIPTION: SEQ ID NO:10:

CTATTCTGGC TAGTTCTGC                                                    19

(2) INFORMATION FOR SEQ ID NO:11:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:11:

AGGTACGCCC GA                                                           12

(2) INFORMATION FOR SEQ ID NO:12:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:12:

CGCCCTGCAG TA                                                           12

(2) INFORMATION FOR SEQ ID NO:13:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:13:

CCATCCGCAC GA                                                           12

(2) INFORMATION FOR SEQ ID NO:14:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:14:

GGTCAGGCAC CA                                                           12

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
            (A) DESCRIPTION: /desc = "SYNTHETIC DNA"

(xi) SEQUENCE DESCRIPTION: SEQ ID NO:15:

CGCCCTGCAG TACCTTCCTG TAAG                                              24

(2) INFORMATION FOR SEQ ID NO:16:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "SYNTHETIC DNA"

(xi) SEQUENCE DESCRIPTION: SEQ ID NO:16:

CGCCCTGCAG TAGAGCACTT CTAT                                              24

(2) INFORMATION FOR SEQ ID NO:17:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "SYNTHETIC DNA"

(xi) SEQUENCE DESCRIPTION: SEQ ID NO:17:

CAATCGCCGT CTTGGTAGCG TA                                                22

(2) INFORMATION FOR SEQ ID NO:18:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "SYNTHETIC DNA"

(xi) SEQUENCE DESCRIPTION: SEQ ID NO:18:

CAATCGCCGT TGAGAAAGTT AAGTA                                             25

(2) INFORMATION FOR SEQ ID NO:19:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "SYNTHETIC DNA"

(xi) SEQUENCE DESCRIPTION: SEQ ID NO:19:

GGTCAGGCAC CATGTACTAG CTGGC                                             25

(2) INFORMATION FOR SEQ ID NO:20:

(i) SEQUENCE CHARACTERISTICS:
            (A) LENGTH: 25 base pairs
            (B) TYPE: nucleic acid
            (C) STRANDEDNESS: single
            (D) TOPOLOGY: linear

```
         (ii) MOLECULE TYPE: other nucleic acid
             (A) DESCRIPTION: /desc = "SYNTHETIC DNA"

(xi) SEQUENCE DESCRIPTION: SEQ ID NO:20:

GGTCAGGCAC CAAGGCCACC ATCTG                                          25

(2) INFORMATION FOR SEQ ID NO:21:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "SYNTHETIC DNA"

(xi) SEQUENCE DESCRIPTION: SEQ ID NO:21:

GCCAGCTGTA CGATGCCATG ACCTTA                                         26

(2) INFORMATION FOR SEQ ID NO:22:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "SYNTHETIC DNA"

(xi) SEQUENCE DESCRIPTION: SEQ ID NO:22:

GCCAGCTGTA CGCCCCGGAA GGAA                                           24

(2) INFORMATION FOR SEQ ID NO:23:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "SYNTHETIC DNA"

(xi) SEQUENCE DESCRIPTION: SEQ ID NO:23:

ACTCACCACG CAGAAACCCA GGC                                            23

(2) INFORMATION FOR SEQ ID NO:24:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "SYNTHETIC DNA"

(xi) SEQUENCE DESCRIPTION: SEQ ID NO:24:

CCTCGACAAG TGAGATGTTG ACC                                            23

(2) INFORMATION FOR SEQ ID NO:25:

(i) SEQUENCE CHARACTERISTICS:
         (A) LENGTH: 23 base pairs
         (B) TYPE: nucleic acid
         (C) STRANDEDNESS: single
         (D) TOPOLOGY: linear
```

(ii) MOLECULE TYPE: other nucleic acid
            (A) DESCRIPTION: /desc = "SYNTHETIC DNA"

(xi) SEQUENCE DESCRIPTION: SEQ ID NO:25:

GCCACATTAT CAAGGCAATA CAC                                              23

(2) INFORMATION FOR SEQ ID NO:26:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "SYNTHETIC DNA"

(xi) SEQUENCE DESCRIPTION: SEQ ID NO:26:

GGCATGACTC ATGCCAGCTG                                                  20

(2) INFORMATION FOR SEQ ID NO:27:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "SYNTHETIC DNA"

(xi) SEQUENCE DESCRIPTION: SEQ ID NO:27:

GTCCCTCCTA GACACCTACA TA                                               22

(2) INFORMATION FOR SEQ ID NO:28:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "SYNTHETIC DNA"

(xi) SEQUENCE DESCRIPTION: SEQ ID NO:28:

GCTCCTGACA GCAAGGTAAG C                                                21

(2) INFORMATION FOR SEQ ID NO:29:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "SYNTHETIC DNA"

(xi) SEQUENCE DESCRIPTION: SEQ ID NO:29:

GAATACTGAG ATTTTTATGA GG                                               22

(2) INFORMATION FOR SEQ ID NO:30:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
    (A) DESCRIPTION: /desc = "SYNTHETIC DNA"

(xi) SEQUENCE DESCRIPTION: SEQ ID NO:30:

CAGGTCATGA CTCATGCTAA                                          20

(2) INFORMATION FOR SEQ ID NO:31:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:31:

AAGGTGTTGC GGCCCTTAAC AACTTCTT                                 28

(2) INFORMATION FOR SEQ ID NO:32:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:32:

AAGGTGTTGC GGAGAGTGTT CTAGAACA                                 28

(2) INFORMATION FOR SEQ ID NO:33:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:33:

ATCGAGCGAA CGTATCAGCT GCG                                      23

(2) INFORMATION FOR SEQ ID NO:34:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:34:

CCTTTCCGAC GTCACTAATC GTGG                                     24

(2) INFORMATION FOR SEQ ID NO:35:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
            (A) DESCRIPTION: /desc = "SYNTHETIC DNA"

(xi) SEQUENCE DESCRIPTION: SEQ ID NO:35:

TTAAATGACA TGATCACCTC TCCC                                              24

(2) INFORMATION FOR SEQ ID NO:36:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:36:

TAACACAGAG GTACCTCACT GTCT                                              24

(2) INFORMATION FOR SEQ ID NO:37:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:37:

CTCCCACTGC ACACCTATTT C                                                 21

(2) INFORMATION FOR SEQ ID NO:38:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:38:

CACCATCTGA AGGAGGTCAA G                                                 21

(2) INFORMATION FOR SEQ ID NO:39:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:39:

CCTTCCTGTA AGGGTTTACA                                                   20

(2) INFORMATION FOR SEQ ID NO:40:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:40:

GAGCACTTCT ATCATTTTTC G                                          21

(2) INFORMATION FOR SEQ ID NO:41:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:41:

GGCGATTCTG CTGCA                                                 15

(2) INFORMATION FOR SEQ ID NO:42:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:42:

GGCGATTCTG CAT                                                   13

(2) INFORMATION FOR SEQ ID NO:43:

(i) SEQUENCE CHARACTERISTICS:
        (A) LENGTH: 599 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:43:

GGCGATTCTG CAAGAGACAC AACGCAGACA AGAAATTTGA ATAACATAAT CGAGAGGGGT    60

TTGCTCTCGA GTCCCTCCTA GACACCTACA TAGCAATTGC TACAATTTCC TAGTGTCCGC   120

AAATATTGTA GGGTTACTAA TGGATTTATT GTTTACATCT GTTGCATTCT TTTATGTAAA   180

TGATGATGAT GAGATTCCAT ATGAATGAGA GTCTTTATAA GCTAAAAATT TAATGGCATG   240

CATTGTATCC CAAGGCAAAT GGTCATGCAG ATGCAATGGA GTACTGAATA AATTAAATTA   300

AACTGGTTTT ACAGACGCTG TTGACAAACA AAATAGGTAA TACCAGAAGC TTACCTTGCT   360

GTCAGGAGCA AATTTTAAAC GAACAGCTTT CCAGTCAGAC ACGTCCTCAT CGGTGCCACC   420

ACTTCCAGTT TCACTGCTTG GTTCCACAGG TTTCTCAAGT ACGTTCTTCC GGAACTTCTC   480

TAGTCTTGCT AGAACCTGAA GGAAACGTTA ACCAGCAAAG TTGGTAATTG GAAACTTAAT   540

TAGCAAATAA TGCTAATGTG AAGAGCAATA CATCAAATTG TTTTATATGC AGAATCGCC    599

(2) INFORMATION FOR SEQ ID NO:44:

(i) SEQUENCE CHARACTERISTICS:
        (A) LENGTH: 629 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:44:

```
GGCGATTCTG CAAGAGACAC AACGCAGACA AGAAATGTGA ATAACATAAT CGAGAGGGGT      60

TTGCTCTCGA GTCCCTCCTA GACACCTACA TAGCAATTGC TACAATTTCC TAGTGTCTGC     120

AAATATTGTA GGGTTACTAA AATATATAGG AAATATCTAA ACGTGTAAAA AATGGATTTA     180

TTGTTTACAT CTGTTGCATT CTTTTATGTA AATGATGATG ACGAGATTCC ATATGAACGA     240

GTCTTTATAA GCTAAAAATT TAATGGCATG CATTGTATCT CAAGGCAAAT GGTCATGCAG     300

ATGCAATGGA GTATGGAATA AATTAAATTA AACTGGTTTC ACAGACGCTG TTGACAAACA     360

AAATAGGTAA TACCAGAAGC TTACCTTGCT GTCAGGAGCA AATTTTAAAC GAACAGCTTT     420

CCAGTCAGAC ACGTCCTCAT CGGTGCCACC ACTTCCAGTT TCACTGCTTG GTTCCACAGG     480

TTTCTCAAGT ACGTTCTTCC GGAACTTCTC TAGTCTTGCT AGAACCTGAA GGAAACATTA     540

ACCAGCAAAG TTGGTAATTG GAAACTTAAT TAGCAAATAA TGCTAATGTG AAGAGCAATA     600

CATCAAATTG TTTTATATGC AGAATCGCC                                      629
```

(2) INFORMATION FOR SEQ ID NO:45:

(i) SEQUENCE CHARACTERISTICS:
        (A) LENGTH: 500 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:45:

```
GGTCAGGCAC CATGTACTAG CTGGCGCGAC ACTCCCACTG CACACCTATT TCCGGTCCGT      60

AGTAGATTAC TTTAACATCT CCCCATTCTA GATCACACCG AATGGGATCC AAGCCCTCTC     120

TGCGCTATAC ATTCTTTACT TTCTGAATGG TTGGGACGAG CCCACTCCAC ATGAGGTGCA     180

TTACTTGTTC GATCTCAGGA CCAACCCCTC TCACAACAAC TCAGGCTTTT TCCACTTCTA     240

TATAGGCATA GGGGGATTAC ATACCTCAAC GGTATTTCTC ATAGGTCGAA TGCCGGGAGG     300

TATCATAAGG GATACTTCCT CACCTTGGAC ATCGAGGCCA ACAAATTTGG GCCTTAACTC     360

GTCGGGGTCC ATTTGAGCGA CCATTGCCTA CTGAGGAGAT GTCAATCGGC CAAGAGTTGG     420

CTAACATGAG TTCTAAAGAT AAGGATGTAA AAGGTTGGTC ACACTTGACC TCCTTCAGAT     480

GGTGGCCTTG GTGCCTGACC                                                500
```

(2) INFORMATION FOR SEQ ID NO:46:

(i) SEQUENCE CHARACTERISTICS:
        (A) LENGTH: 488 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:46:

```
CGCCCTGCAG TACCTTCCTG TAAGGGTTTA CAGGGGACTT GATACAACCT CTAGGTGCAA      60

TCAAGTTAGC CCTCACAATG GGAGAGAAAC CAAGACAAAC CACTATAATG ACAAACTTTG     120

TCGTGGTAGA TTGTGCCTCA GCCTTAAATG CGGTATTAGA AAGACCTTCC CTAAGAGAAT     180

TGAAGGGAAT AACCTCAGTA TAACACTTGG CCATAAAATT CCCAACTCTT GGAGGAATAG     240

CGAGCGTGAA AGGGGAATAG AAGGAAGCAA GGGAATGTTA TAACACGTCC CTCCACACAG     300
```

```
TCATGAAACT GCCATTACCC ATGGTGATGG TGGTGCATGG AGGTGCAAAC TCACATGACT        360

TAGACCCTCG AGTTGTTGAG GAGATCAGAA TCAAAATGGA TAACAGAGAG ATAAATGAGC        420

TATGCCTAAA AAAATCAGAA ATTAGAAGAG CAGTGCGAAA AATGATAGAA GTGCTCTACT        480

GCAGGGCG                                                                 488

(2) INFORMATION FOR SEQ ID NO:47:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:47:

GGTCAGGCAC CA                                                             12

(2) INFORMATION FOR SEQ ID NO:48:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:48:

CGCCCTGCAG TA                                                             12
```